(12) United States Patent
Hergeth

(10) Patent No.: US 7,832,061 B2
(45) Date of Patent: Nov. 16, 2010

(54) AIR GUIDANCE AT A CELLULOSE OPENER

(76) Inventor: Hubert A. Hergeth, Alznach 2, CH-6343 Rotkreuz (CH)

( * ) Notice: Subject to any disclaimer, the term of this patent is extended or adjusted under 35 U.S.C. 154(b) by 550 days.

(21) Appl. No.: 10/998,770

(22) Filed: Nov. 29, 2004

(65) Prior Publication Data

US 2005/0144759 A1 Jul. 7, 2005

(30) Foreign Application Priority Data

Nov. 28, 2003 (DE) .............................. 103 56 363

(51) Int. Cl.
*D04H 1/00* (2006.01)
(52) U.S. Cl. ........................................ 19/303; 19/148
(58) Field of Classification Search ................. 19/148, 19/308, 107; 604/374
See application file for complete search history.

(56) References Cited

U.S. PATENT DOCUMENTS

| | | | | |
|---|---|---|---|---|
| 3,699,202 A | * | 10/1972 | Verbestel | 264/109 |
| 3,728,872 A | * | 4/1973 | Thore | 66/9 B |
| 3,973,291 A | * | 8/1976 | Kolbach | 19/148 |
| 4,198,725 A | | 4/1980 | Trützschler | 15/306 B |
| 4,592,708 A | * | 6/1986 | Feist et al. | 425/80.1 |
| 5,097,574 A | * | 3/1992 | Hertel et al. | 28/105 |
| 5,245,728 A | * | 9/1993 | Rupp et al. | 19/148 |
| 5,515,578 A | * | 5/1996 | Mondini et al. | 19/115 B |
| 5,778,492 A | * | 7/1998 | Thiessen et al. | 19/107 |
| 6,080,909 A | * | 6/2000 | Osterdahl et al. | 604/368 |
| 6,475,315 B1 | * | 11/2002 | Kean et al. | 156/62.2 |
| 6,497,009 B2 | * | 12/2002 | Geisen et al. | 19/296 |
| 2003/0037532 A1 | * | 2/2003 | Heinz et al. | 57/352 |

* cited by examiner

*Primary Examiner*—Shaun R Hurley
(74) *Attorney, Agent, or Firm*—The Webb Law Firm

(57) ABSTRACT

Air guidance between a cellulose opener and a diaper machine is characterized in that the air used for removal and conveying to the diaper machine is guided back to the opener and is again used for fiber conveying. Specifically, air guidance achieved by designing the fiber opener in such manner that the exhaust air from the diaper machine which has conveyed the fibers to the diaper machine is guided back to the fiber opener and serves to remove the fibers from the opener roller.

4 Claims, 1 Drawing Sheet

AIR GUIDANCE AT A CELLULOSE OPENER

BACKGROUND OF THE INVENTION

In installations for the production of sanitary articles hammer mills are used to break up cellulose webs. The cellulose is used in suction pillows.

Instead of hammer mills, openers have been used in recent times where a roller surrounded by saw teeth such as is used in the textile industry opens the cellulose web.

The opener consists essentially of a presentation device to the opener roller and a housing. Air guidance is important at the opener roller in order to convey the fibers away. Air aspired from the environment flows along the roller.

This is more difficult than with hammer mills. The removed fibers are conveyed in the same air stream to the sanitary machine where they are either separated from the air stream to be placed in intermediary storage, or are formed into a suction pillow directly at a forming wheel.

On the circumference of a forming wheel are depressions at the bottom of which is a sieving surface. The air together with the fibers is pulled into the depression, the fibers are deposited in the depression and the air is again pulled through the sieving surfaces and reaches a filter. The installation and operating costs of a filter are considerable. The accumulation is mainly of short fibers and dust whose reintegration into the process is problematic.

SUMMARY OF THE INVENTION

It is the object of the invention to design an opener and the process in such manner that the filter is no longer necessary and so that all the fibers are integrated into the product. This is achieved by designing the fiber opener in such manner that the exhaust air from the diaper machine which has conveyed the fibers to the diaper machine is guided back to the fiber opener and serves to remove the fibers from the opener roller.

DETAILED DESCRIPTION OF THE INVENTION

Figure 1:
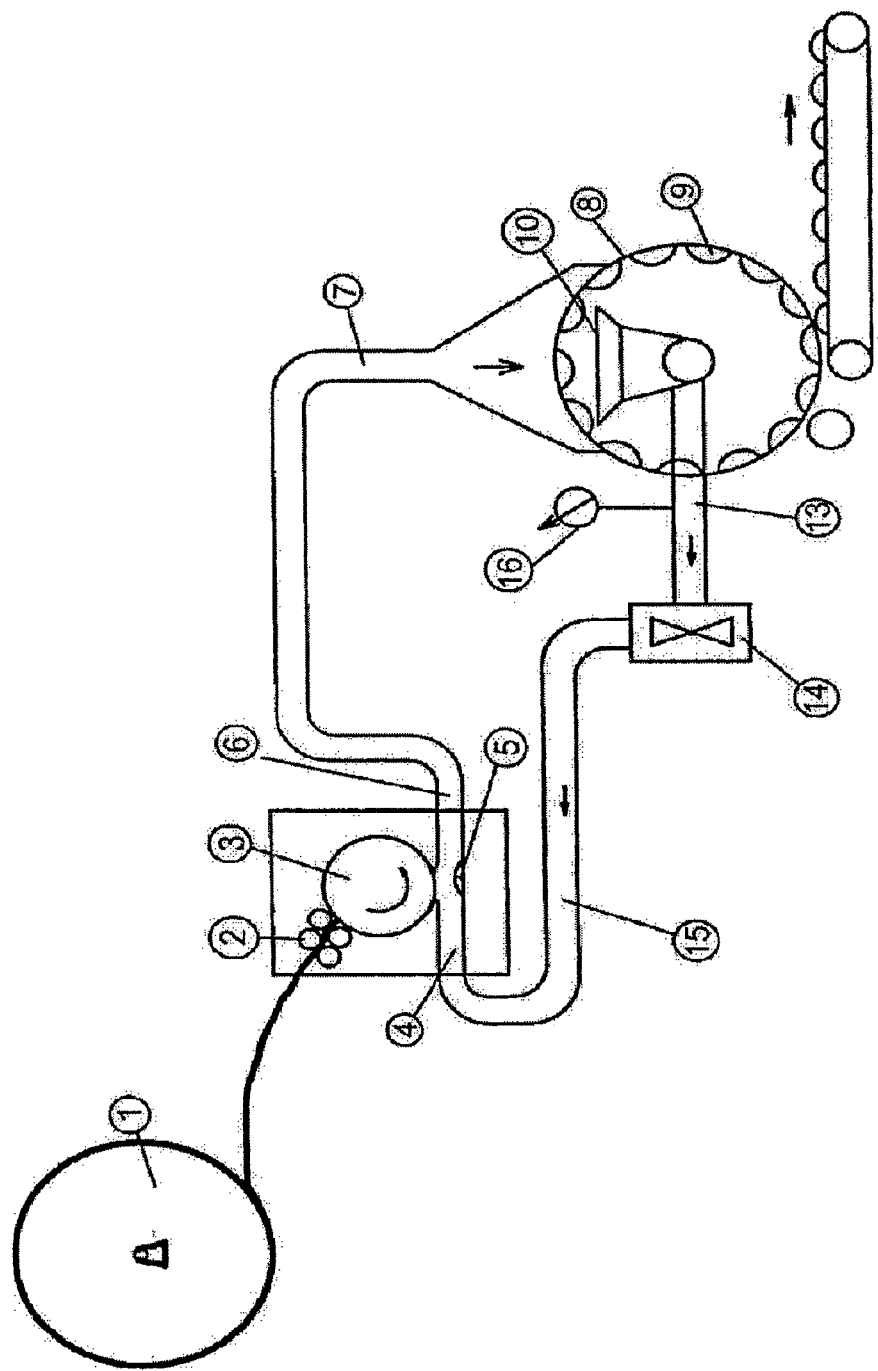
FIG. 1 is a schematic illustration of an air guidance installation in accordance with the present invention.

The application is described through FIG. 1.

The cellulose web is pulled of a roll with a cellulose web 1 by means of feed rollers and is conveyed to an opener roller 3. The opener roller 3 is preferably equipped with a saw tooth garniture.

The flakes opened by the saw tooth roller are taken over by an air stream which flows through an approach shaft 4 and past the saw tooth roller at the removal zone and are conveyed through an evacuation conduit 7 out of the funnel 6 of the opener housing. In the area of air decrease the air current is accelerated by an air guiding element 5 across from the saw tooth roller.

The fibers reach an intermediate storage or directly the forming wheel 8.

The fibers accumulate in pockets 9 so that a pillow is formed. The air is pulled through the pillow and through a perforation in the forming wheel out of the forming wheel by means of a suction funnel 10 and is conveyed via a pipe line 13 to a ventilator 14.

An air sensor 16 monitors the suction conduit 13 and adjusts the ventilator if necessary to keep the pillow formation constant.

A pipeline 15 conveys the air to the opener aggregate.

The invention claimed is:

1. An installation for production of sanitary articles comprising:
   an opener roller for receiving a cellulose web and pulling cellulose fibers from the cellulose web, the opener roller including an outlet coupled to an air guiding element;
   a diaper machine comprising an inlet for directing the cellulose fibers to a forming wheel with a perforation and pockets in which the cellulose fibers are accumulated to form a pillow, a first outlet for receiving the pillows, and a suction funnel coupled to a second outlet;
   at least one ventilator coupled to the second outlet; and
   a pipeline coupled between the at least one ventilator and the inlet of the diaper machine and configured and coupled to the air guiding element to receive cellulose fibers from the opener roller,
   wherein an air stream, after being pulled through the forming wheel of the diaper machine, flows into the suction funnel of the diaper machine, out of the second outlet, through the at least one ventilator, and back to the opener roller via the air guiding element where the air stream again takes off fibers.

2. The installation as in claim 1, wherein the air stream is measured and in that the air stream is influenced automatically in order to achieve constant air flow conditions at the forming wheel.

3. The installation as in claim 2, wherein the air stream is influenced by a throttle, a supplier or remover of air or by an adjustment of rotational seed.

4. The installation as in claim 1, wherein in the opener roller the air is subjected to a change in air speed in the area of fiber removal in the opener roller.

* * * * *

UNITED STATES PATENT AND TRADEMARK OFFICE
CERTIFICATE OF CORRECTION

| | | |
|---|---|---|
| PATENT NO. | : 7,832,061 B2 | Page 1 of 1 |
| APPLICATION NO. | : 10/998770 | |
| DATED | : November 16, 2010 | |
| INVENTOR(S) | : Hergeth | |

It is certified that error appears in the above-identified patent and that said Letters Patent is hereby corrected as shown below:

Column 2, line 47, Claim 3, "rotational seed" should read -- rotational speed --

Signed and Sealed this
Twenty-second Day of March, 2011

David J. Kappos
*Director of the United States Patent and Trademark Office*